United States Patent
Seong et al.

(10) Patent No.: US 9,361,685 B2
(45) Date of Patent: Jun. 7, 2016

(54) APPARATUS AND METHOD FOR ACQUIRING MULTI-PARAMETRIC IMAGES IN MAGNETIC RESONANCE IMAGING DEVICE

(71) Applicant: Samsung Electronics Co., Ltd., Suwon-si (KR)

(72) Inventors: Yeong-Kyeong Seong, Yongin-si (KR); Jong-Ha Lee, Yongin-si (KR); Won-Hee Choe, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 108 days.

(21) Appl. No.: 14/094,019

(22) Filed: Dec. 2, 2013

(65) Prior Publication Data

US 2014/0153807 A1 Jun. 5, 2014

(30) Foreign Application Priority Data

Nov. 30, 2012 (KR) .......................... 10-2012-0138089

(51) Int. Cl.
| | | |
|---|---|---|
| *G06K 9/00* | (2006.01) | |
| *G06T 7/00* | (2006.01) | |
| *A61B 5/055* | (2006.01) | |
| *G01R 33/56* | (2006.01) | |

(52) U.S. Cl.
CPC .......... *G06T 7/0016* (2013.01); *G01R 33/5608* (2013.01); *A61B 5/055* (2013.01); *G01R 33/5602* (2013.01); *G06T 2207/10088* (2013.01); *G06T 2207/30004* (2013.01)

(58) Field of Classification Search
CPC ...................................................... G06T 7/00
USPC ............................................................ 382/100
See application file for complete search history.

(56) References Cited

U.S. PATENT DOCUMENTS 8,185,511 B2  5/2012  Agnihorti et al.
8,188,743 B2  5/2012  Sugiura
(Continued)

FOREIGN PATENT DOCUMENTS

JP    2012-016480    1/2012
KR  10-2005-0055599  6/2005
(Continued)

OTHER PUBLICATIONS

Pinto, Peter A., et al. "Magnetic resonance imaging/ultrasound fusion guided prostate biopsy improves cancer detection following transrectal ultrasound biopsy and correlates with multiparametric magnetic resonance imaging." The Journal of urology 186.4 (2011): 1281-1285.*

(Continued)

*Primary Examiner* — Gregory F Cunningham
(74) *Attorney, Agent, or Firm* — NSIP Law

(57) ABSTRACT

There are provided an apparatus and a method for acquiring multi-parametric images from an MRI device. In one general aspect, the apparatus for acquiring multi-parametric images includes an image analyzer configured to determine a significance level of each of a plurality of multi-parametric images relating to a disease, and to determine an acquisition order of the multi-parametric images relating to the disease; and a model constructer configured to construct an acquisition model of the multi-parametric images based on the acquisition order and the multi-parametric images to be used in diagnosing the disease.

27 Claims, 9 Drawing Sheets

(56) References Cited

U.S. PATENT DOCUMENTS

| | | |
|---|---|---|
| 8,194,937 B2 | 6/2012 | Chen |
| 8,198,891 B2 | 6/2012 | Sacolick et al. |
| 8,208,703 B2 | 6/2012 | Kawagishi et al. |
| 2005/0154292 A1 | 7/2005 | Tank |
| 2011/0201917 A1 | 8/2011 | Li et al. |
| 2013/0129168 A1* | 5/2013 | Ross ........................... 382/128 |
| 2013/0211230 A1* | 8/2013 | Sperling ............... A61B 8/468 600/410 |
| 2015/0142460 A1* | 5/2015 | Doyle ............... H03M 7/3059 705/2 |

FOREIGN PATENT DOCUMENTS

| | | |
|---|---|---|
| KR | 10-2009-0019837 | 2/2009 |
| KR | 10-2011-0082067 | 7/2011 |

OTHER PUBLICATIONS

Turkbey, Baris, et al. "Documenting the location of systematic transrectal ultrasound-guided prostate biopsies: correlation with multi-parametric MRI." Cancer imaging: the official publication of the International Cancer Imaging Society 11 (2011): 31.*

* cited by examiner

APPARATUS AND METHOD FOR ACQUIRING MULTI-PARAMETRIC IMAGES IN MAGNETIC RESONANCE IMAGING DEVICE

CROSS-REFERENCE TO RELATED APPLICATIONS

This application claims the benefit under 35 U.S.C. §119(a) of Korean Patent Application No. 10-2012-0138089, filed on Nov. 30, 2012, the entire disclosure of which is incorporated herein by reference for all purposes.

BACKGROUND

1. Field

The following description relates to an apparatus and a method for acquiring multi-parametric images on the basis of disease from Magnetic Resonance Imaging (MRI) device.

2. Description of the Related Art

Magnetic Resonance Imaging (MRI) is a medical imaging technique used in radiology to visualize internal structures of the body in detail. MRI makes use of the property of nuclear magnetic resonance (NMR) to image nuclei of atoms inside of the body. Proton magnetic resonance refers to excitation and relaxation by electromagnetic wave of a proton within a positive field, and an MR signal refers to electromagnetic wave relaxed by the proton, and an MRI image is a result of visualizing the MR signal. There are various MRI techniques using different variables, and a number of contrast-type images may be acquired by adjusting the variables. Various types of contrast, including proton density, T1 relaxation time, T2 relaxation time, magnetic susceptibility, chemical shift, chemical exchange, diffusion of water molecule, and elasticity, may weight an MRI image. In addition, each contrast-type image makes use of a specific variable. Thus, many images of diverse variables can be acquired using a method for acquiring multi-parametric images where variables of an image are adjusted.

As such, an MRI device may acquire multi-parametric images of various physical properties to diagnose a disease by analyzing the multi-parametric images, and thus the accuracy of diagnosis may improve. However, the MRI device still heavily depends on a heuristic model to obtain contrast-type images optimized in diagnosing a specific disease.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect an apparatus for acquiring multi-parametric images, the apparatus including an image analyzer configured to determine a significance level of each of a plurality of multi-parametric images relating to a disease, and to determine an acquisition order of the multi-parametric images and the multi-parametric images to be used in diagnosing the disease; and a model constructer configured to construct an acquisition model of the multi-parametric images based on the acquisition order and the multi-parametric images to be used in diagnosing the disease.

The apparatus for acquiring multi-parametric images may include an image acquirer configured to acquire the multi-parametric images using the constructed acquisition model of the multi-parametric images.

The apparatus for acquiring multi-parametric images may include a model store configured to store the acquisition model of the multi-parametric images.

The image analyzer may include a Region of Interest (ROI) extractor configured to extract an ROI from each of the plurality of multi-parametric images, and a feature extractor configured to extract a feature from the ROI; and the image analyzer may be further configured to determine the significance level of each of the plurality of multi-parametric images based on the extracted features.

The apparatus for acquiring multi-parametric images may include a feature analyzer configured to determine whether the extracted feature is significant.

The apparatus for acquiring multi-parametric images may include an image optimizer configured to normalize the ROI; and the feature extractor may extract the feature from the normalized ROI.

The image optimizer may be further configured to remove noise from the normalized ROI, and the feature extractor extracts the feature from the normalized ROI where the noise is removed.

The features may comprise one or more pieces of information about shape, brightness, or boundary.

The image analyzer may determine the significance level of each of the plurality of multi-parametric images based on a number of significant features in each multi-parametric image for diagnosing the disease.

The number of significant features may be determined based on frequency of the features in multi-parametric images of patients suffering from a same disease.

The image analyzer may determine that the multi-parametric image is to be used in diagnosing the disease when the number of significant features in each multi-parametric image exceeds a threshold.

The apparatus for acquiring multi-parametric images may include an image store configured to store the multi-parametric images.

In another general aspect, a method for acquiring multi-parametric images, the method including determining, at an image analyzer, a significance level of each of a plurality of multi-parametric images relating to a disease; determining, based on the determined significance levels, an acquisition order of the multi-parametric images and the multi-parametric images to be used in diagnosing the disease; and constructing an acquisition model of the multi-parametric images based on the acquisition order and the multi-parametric images to be used in diagnosing the disease.

The method for acquiring multi-parametric images may include acquiring the multi-parametric images for diagnosing the disease, by using the constructed acquisition model of the multi-parametric images.

The determining of the significance level may include extracting a ROI from each of the multi-parametric images; extracting a feature from the ROI; and determining the significance level of each of the multi-parametric images based on the extracted feature.

The determining of the significance level may include normalizing the ROI, and extracting the feature from the normalized ROI.

The determining of the significance level may include removing noise from the normalized ROI, and extracting the feature from the normalized ROI where noise is removed.

The features may include one or more pieces of information about shape, brightness, or boundary.

The determining of a significance level may include determining a significance level of each of the plurality of multiparametric images based on a number of significant features in each multi-parametric image.

The number of significant features may be determined based on frequency of the features in multi-parametric image of multiple patients suffering from a same disease.

The determining of the significance level may include using each multi-parametric image in diagnosing the disease when the number of significant features in the multi-parametric image exceeds a threshold.

The determining an acquisition order may include assigning a weighted value to each of the multi-parametric images; determining the acquisition order of the multi-parametric images by multiplying the weighted value by the number of significant features in the multi-parametric image.

In another general aspect, an apparatus for acquiring multi-parametric images, the apparatus including an image analyzer configured to determine an acquisition order of the multi-parametric images and the multi-parametric images to be used in diagnosing the disease; a model constructer configured to construct an acquisition model of the multi-parametric images based on the acquisition order and the multi-parametric images to be used in diagnosing the disease; and an image acquirer configured to acquire the multi-parametric images based on the acquisition model.

A model store may be configured to store the acquisition model of the multi-parametric images.

The image analyzer may include a Region of Interest (ROI) extractor configured to extract an ROI from each of the plurality of multi-parametric images; a feature extractor configured to extract a feature from the ROI; and a feature analyzer configured to determine whether the extracted feature is significant.

The image analyzer may be configured to determine a significance level of each of the plurality of multi-parametric images based on the based on a number of significant features in each multi-parametric image; and the image analyzer may be configured to determine the acquisition order and the multi-parametric images to be used in diagnosing the disease based on the significance level of each of the plurality of multi-parametric images.

The apparatus for acquiring multi-parametric images may include an image optimizer configured to normalize the ROI; and the feature extractor extracts the feature from the normalized ROI.

Other features and aspects will be apparent from the following detailed description, the drawings, and the claims.

Figure 1:
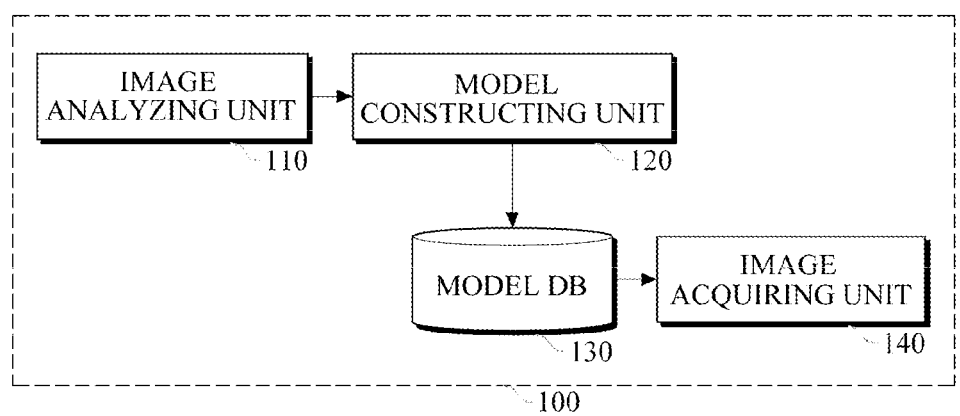
FIG. 1 is a diagram illustrating an example of multi-parametric image acquisition apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will suggest themselves to those of ordinary skill in the art. In addition, descriptions of well-known functions and constructions may be omitted for increased clarity and conciseness.

FIG. 1 is a diagram illustrating an apparatus for acquiring multi-parametric images. Referring to FIG. 1, the apparatus for acquiring multi-parametric images 100 includes an image analyzing unit 110 and a model constructing unit 120. The image analyzing unit 110 determines significant levels of acquired multi-parametric images relating to a disease by analyzing the multi-parametric images. If significance levels are determined, an acquisition order of the multi-parametric images relating to the disease and multi-parametric images to be used in diagnosing a lesion of the disease are determined based on the significance levels. Here, a significance level indicates a suitability of each multi-parametric image with respect to a specific disease. The significance level indicates the suitability of a contrast-type multi-parametric image of a specific variable to represent a disease. Significance level can be determined by a variety of methods, and some of which will be described with reference to FIG. 2.

When the image analyzing unit 110 determines the acquisition order of the multi-parametric images and the multi-parametric images to be used in diagnosing the disease, the model constructing unit 120 constructs an acquisition model of the multi-parametric images relating to the disease.

According to another example, the apparatus for acquiring multi-parametric images 100 may further include a model Database (DB) 130 and an image acquiring unit 140. The model constructing unit 120 may store the constructed acquisition model of the multi-parametric images in the model DB 130. The constructed acquisition model can be used for diagnosing a lesion with respect to the disease. To diagnose a lesion with respect to a specific disease, the image acquiring unit 140 may acquire desired multi-parametric images from an MRI device using a corresponding acquisition model stored in the model DB 130.

The apparatus for acquiring multi-parametric images 100 may rapidly acquire multi-parametric images required for diagnosing the specific disease. Thus, the apparatus for acquiring multi-parametric images 100 may be used in various ways, such as a system for diagnosing whether a lesion is benign or malignant based on a two- or three-dimensional medical image, a system for providing lesion diagnosis result, or a remote clinic system.

Figure 2:
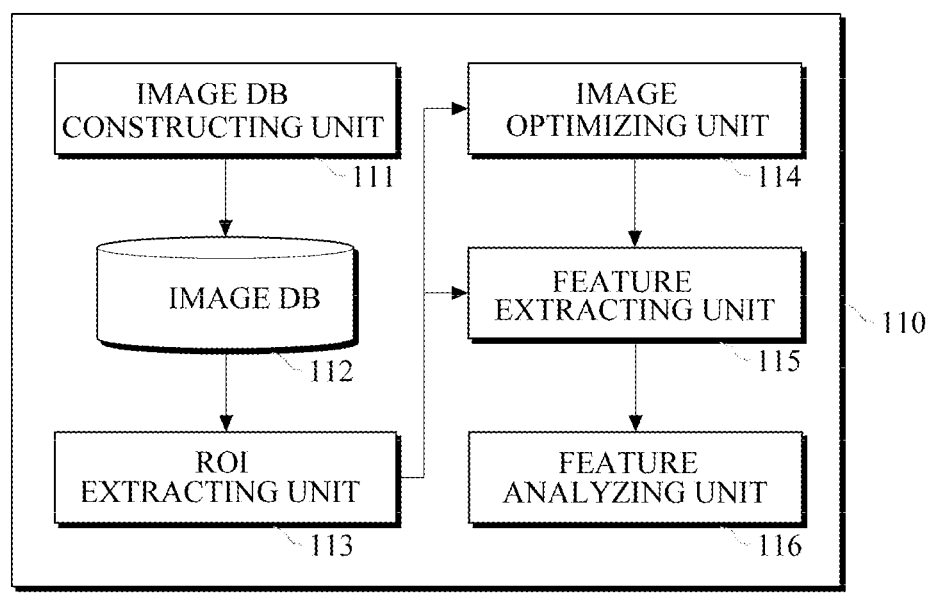
FIG. 2 is a diagram illustrating an example of an image analyzing unit of the apparatus for acquiring multi-parametric images shown in FIG. 1.

FIG. 2 is a diagram illustrating an example of the image analyzing unit 110 of the apparatus for acquiring multi-parametric images 100 shown in FIG. 1. FIGS. 3A to 3E are diagrams illustrating examples of determining an acquisition order of multi-parametric images. Configuration of the image analyzing unit 110 will be described with reference to FIG. 2 and FIGS. 3A to 3E. The image analyzing unit 110 may include an image DB constructing unit 111, an image DB 112, a Region of Interest (ROI) extracting unit 113, an image optimizing unit 114, a feature extracting unit 115, and a feature analyzing unit 116.

Figure 3A:
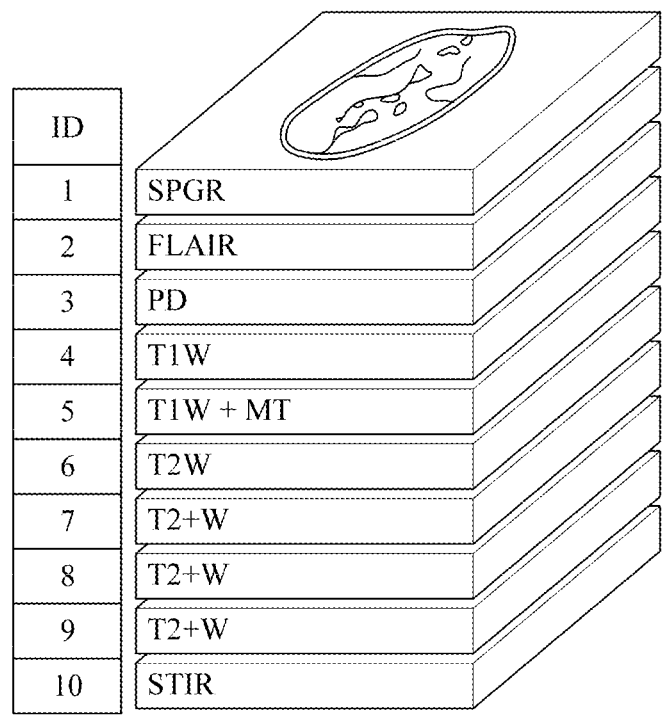
FIGS. 3A to 3E are diagrams illustrating examples of determining the acquisition order of multi-parametric images.

With different contrast-type multi-parametric images are acquired through an MRI device based on disease and stored in the image DB 112. The image DB constructing unit 111 may construct a multi-parametric image DB based on many different criteria, such as, for example, different types of disease. FIG. 3A shows examples of ten multi-parametric images ID 1 through ID 10 with respect to a specific disease that are acquired from an MRI device and are stored in the image DB 112.

Figure 3B:
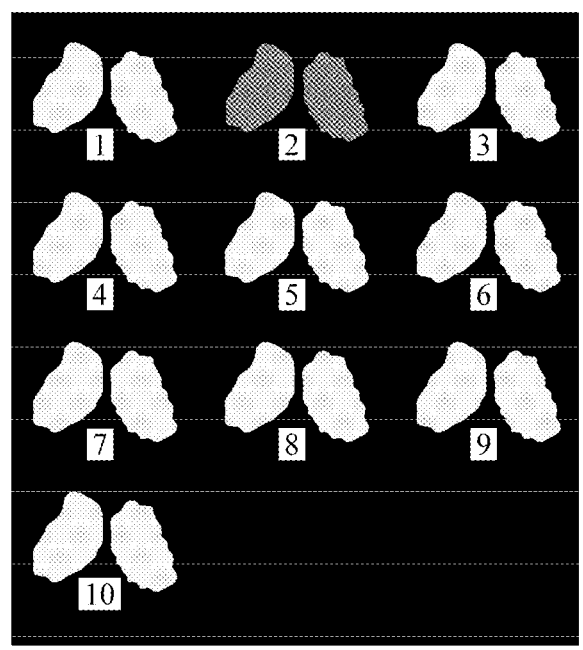

The ROI extracting unit 113 extracts a ROI, i.e., a lesion area, from each multi-parametric image stored in the image DB 112. FIG. 3B shows ten ROI extracted from ten multi-parametric images ID 1 through ID 10. The ROI extracting unit 113 may extract a ROI from each of multi-parametric images relating to a specific disease using a ROI extracting algorithm. Since those skilled in the art may use any ROI extracting algorithm, detailed description about the algorithm is not provided.

Figure 3C:
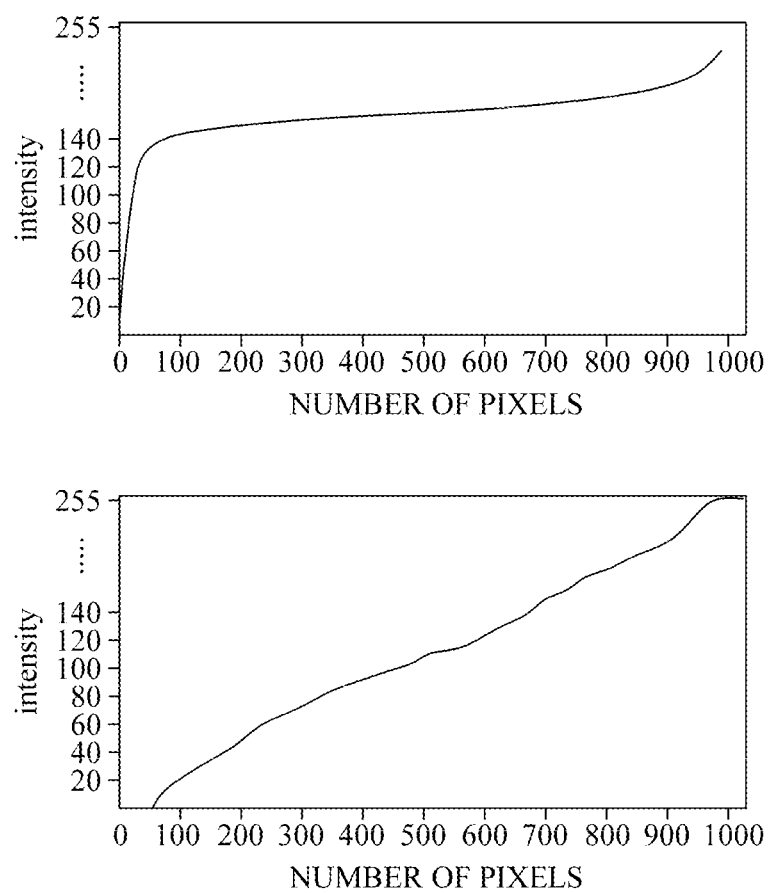
Figure 3D:
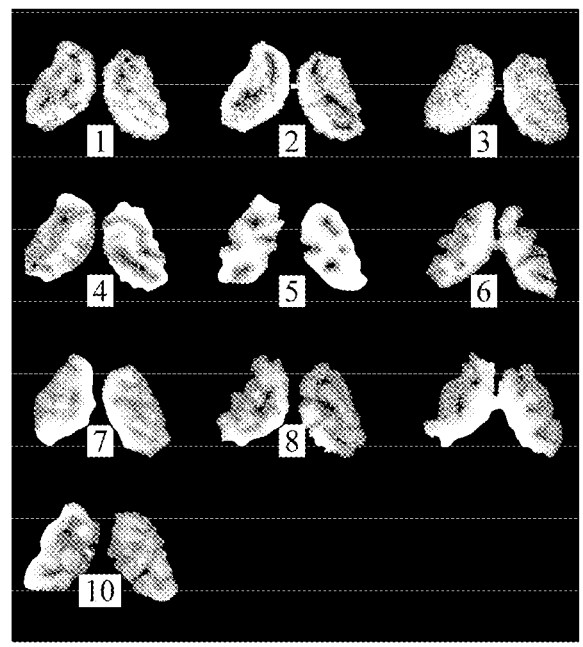

The image optimizing unit 114 may normalize the ROI extracted from each of the multi-parametric image using a scheme, such as for example a histogram equalization scheme. For example, brightness may be unequal between multi-parametric images, so the image optimizing unit 114 may normalize the ROI extracted from each of the multi-parametric images to make the brightness equal, thereby improving diagnosis accuracy. FIG. 3C illustrates graphs to show a change caused by the normalization of a ROI included in a multi-parametric image. In FIG. 3C, the upper graph is a graph of any one of the multi-parametric images shown in FIG. 3B where normalization is not performed. In the upper graph, the number of pixels in the ROI is closer to 0, so the ROI may look darker than other regions. If normalization is performed on a ROI of unequal brightness, brightness may become equal, as shown in the lower graph of FIG. 3C. The lower graph in FIG. 3C is a graph about a multi-parametric image whose ROI has been normalized to make brightness equal. Furthermore, the image optimizing unit 114 may remove noise from the normalized ROI. FIG. 3D is a normalized version of FIG. 3B.

The feature extracting unit 115 extracts a feature from a ROI. Here, features may include, but is not limited to, one or more piece of information about shape, brightness and boundary of the ROI, as shown in the following Table 1.

TABLE 1

| Shape | Brightness | Boundary |
|---|---|---|
| Circular (a) | Bright (b) | Clear Boundary (c) |
| Rectangular (a') | Dark (b') | Blurred boundary(c') |
| Regular (a") | Equal Texture (b") | ... |
| ... | ... | ... |

The feature analyzing unit 116 may determine a significance level of each of the multi-parametric images relating to a specific disease based on the extracted features. When significance levels of the multi-parametric images are determined, the feature analyzing unit 116 may determine an acquisition order of the multi-parametric images relating to the specific disease and multi-parametric images to be used in diagnosing the specific disease.

The feature analyzing unit 116 may analyze a feature extracted from each of multi-parametric images and determine which feature is significant for diagnosing a specific disease. As example for determining which feature extracted from which multi-parametric image is significant for diagnosing a specific disease is shown in Tables 2 and 3 below:

TABLE 2

| | Patient 1 | Patient 2 | Patient 3 |
|---|---|---|---|
| Image 1 | a, b, c | a, b', c | a, b", c' |
| Image 2 | a', b, c | a", b, c | a', b", c' |
| Image 3 | a', b, c' | a, b', c | a", b", c' |

TABLE 3

| Feature | a | a' | a" | b | b' | b" | c | c' |
|---|---|---|---|---|---|---|---|---|
| Image 1 | 3 | 0 | 0 | 1 | 1 | 1 | 2 | 1 |
| Image 2 | 0 | 2 | 1 | 2 | 0 | 1 | 2 | 1 |
| Image 3 | 1 | 1 | 1 | 1 | 1 | 1 | 1 | 2 |

Table 2 shows examples of features that are extracted from each of three multi-parametric images with respect to three patients suffering from the same disease. Table 3 illustrates the frequency of extraction of each feature from the three multi-parametric images of the three patients. In the non-exhaustive example illustrated in tables 2 and 3 each of the three patients has three medical images, however, different number of multi-parametric images and patients may be utilized.

When the frequency of a feature exceeds a predetermined reference level, it may be determined that the feature is significant in a corresponding multi-parametric image. For example, when the predetermined reference level is 50%, it may be determined that a (100%) and c (about 67%) are significant in a multi-parametric image 1, that a' (about 67%), b (about 67%) and c (about 67%) are significant in a multi-parametric image 2, and that c' (about 67%) is significant in a multi-parametric image 3.

The feature analyzing unit 116 may determine a significance level of each multi-parametric image based on the number of significant features in the multi-parametric image, i.e., higher significance level is assigned to multi-parametric image having greater number of significant features. Thus, image 2 has the highest significance level among images 1 to 3, whereas image 3 has the least significance level. If two images have the same number of significant features, a higher significant level may be assigned to a multi-parametric image in which a sum of frequency of all significant features is greater than that of the other multi-parametric image.

Figure 3E:
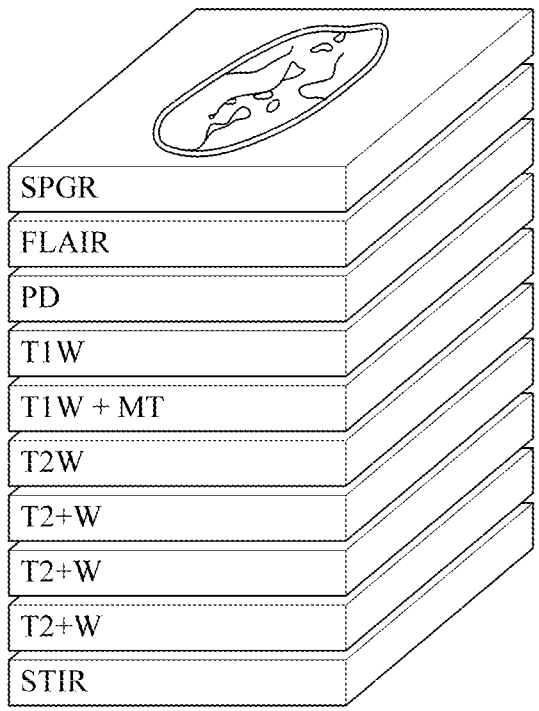

FIG. 3E shows an acquisition order of multi-parametric images based on significant levels determined in the above manner. The feature analyzing unit 116 may determine multi-parametric images to be used in diagnosing a specific disease, based on significance levels of each multi-parametric image (i.e., a value reflecting the number of significant features of each multi-parametric image). In another non-exhaustive example, the feature analyzing unit 116 may assign a weighted value to each of the multi-parametric images relating to the specific disease based on general MRI information, multiply the weighted value by the number of significant features in the multi-parametric image, and then determine the acquisition order of the multi-parametric images relating to the disease based on the multiplied result.

If a significance level of the multi-parametric image exceeds a predetermined threshold with respect to the disease, the feature analyzing unit 116 may determine that the multi-parametric image is to be used in diagnosing a lesion with respect to the disease. The number of multi-parametric images to be used in diagnosing a lesion, such as, for example, five images for a spinal herniated disc and three images for a neck herniated disc, may be determined in advance in consideration of time, costs, and other factors required for diagnosing the disease. The predetermined number of multi-parametric images may be determined to be significant for diagnosing the disease.

Figure 4:
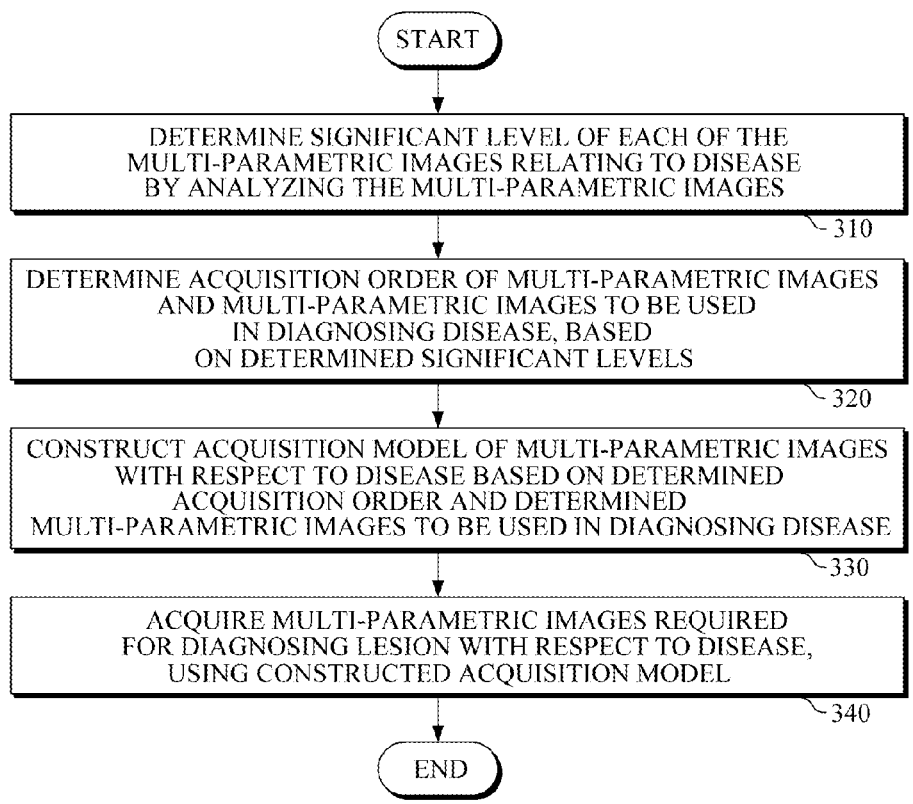
FIG. 4 is a diagram illustrating an example of a method for acquiring multi-parametric images.
Figure 5:
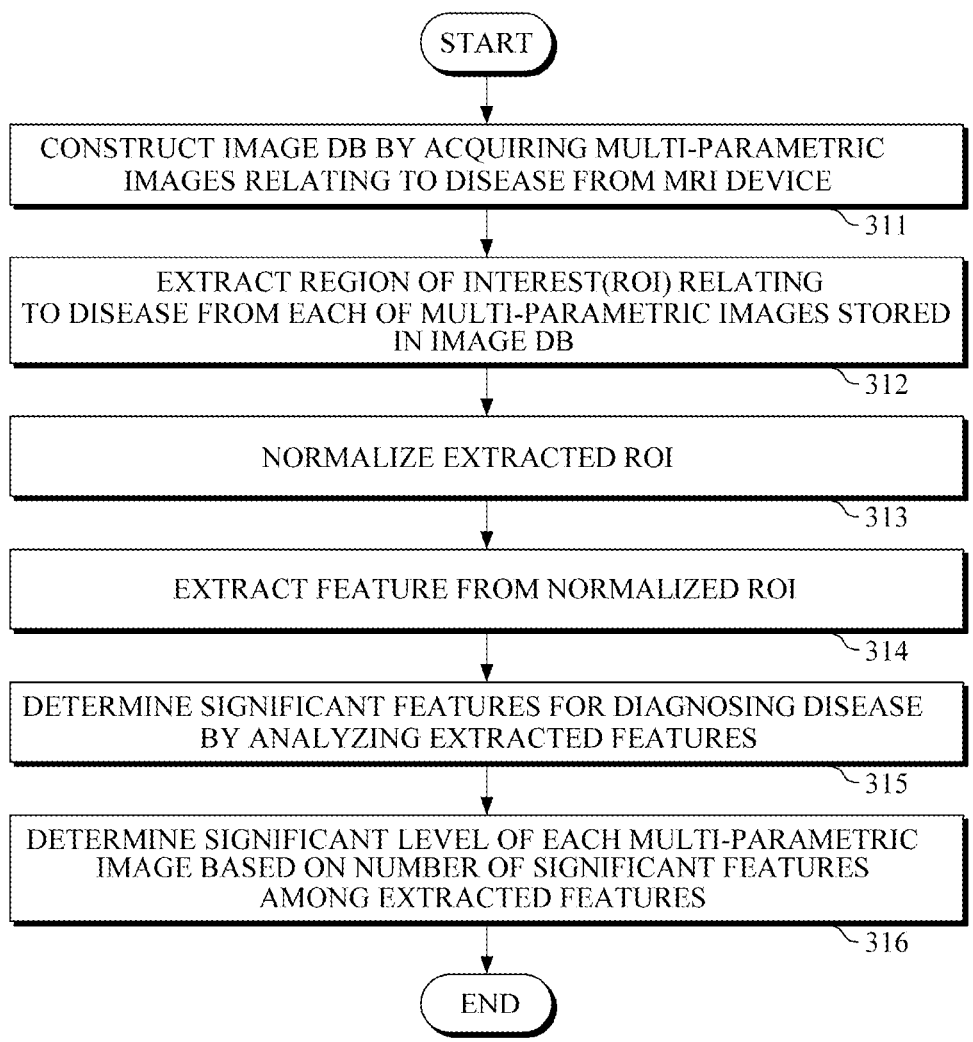
FIG. 5 is a diagram illustrating an example of a process of determining significance levels of multi-parametric images according to the method of FIG. 4.

In a non-exhaustive example, FIG. 4 illustrates a method for acquiring multi-parametric images using the apparatus for acquiring multi-parametric images 100 of FIG. 1 and FIG. 5 illustrates a significance level determining operation 310 in the method for acquiring multi-parametric images according to the method of FIG. 4. The operations in FIGS. 4 and 5 may be performed in the sequence and manner as shown, although the order of some operations may be changed or some of the operations omitted without departing from the spirit and scope of the illustrative examples described. Many of the operations shown in FIGS. 4 and 5 may be performed in parallel or concurrently.

In 301, the apparatus for acquiring multi-parametric images 100 analyzes the multi-parametric images to determine a significance level of each of multi-parametric images acquired with respect to a specific disease.

Referring to FIG. 5, a multi-parametric image DB may be constructed such that various contrast-type multi-parametric images relating to the specific disease are acquired from an MRI device by adjusting variables, and in 311, the acquired multi-parametric images are stored in the image DB 112. In 312, a ROI is extracted from each of the multi-parametric images stored in the image DB 112 in operation 312. In 313, the ROI extracted from each of the multi-parametric images is normalized and the normalized ROI is used to diagnose the disease so that a lesion may be diagnosed with high accuracy with respect to the disease.

In 314, features are extracted from each ROI. Examples of features extracted in the above manner are presented in Table 1. However, Table 1 is merely exemplary, and various other features may be extracted.

In 315, the extracted features are analyzed to determine which feature extracted from which multi-parametric image is appropriate and significant for diagnosing the disease. As described above with reference to Tables 2 and 3, if a feature is commonly found among multiple patients suffering from the same disease, the feature may be determined to be a significant feature in a corresponding multi-parametric image for diagnosing the disease.

In 316, a significance level of each of the multi-parametric images is determined based on the number of the significant features. For example, the more number of significant features a multi-parametric image has, the greater significance level is assigned thereto. In another example, the greater sum of frequency of significant features a multi-parametric image has, the greater significance level is assigned thereto.

Referring to FIG. 4, in 320, if the significance levels of the multi-parametric images relating to the disease are determined, an acquisition order of the multi-parametric images and multi-parametric images to be used in diagnosing the disease may be determined. For example, if an arbitrary number is set in consideration of time and costs required for diagnosing a disease and the number of significant features in a multi-parametric image exceeds the arbitrary number, it may be determined that such a multi-parametric image is to be used in diagnosing the disease. In another example, if a threshold is predetermined to be an arbitrary value and the number of significant features in a multi-parametric image exceeds the predetermined threshold, it may be determined that the multi-parametric image is to be used in diagnosing a disease.

In 330, if the acquisition order of the multi-parametric images relating to the disease and the multi-parametric images to be used in diagnosing the disease are determined, an acquisition model of the multi-parametric images relating to the disease may be constructed. The constructed acquisition model may be stored in the model DB 130 to be used for diagnosing a lesion with respect to the disease.

In 340, in the event of the need to diagnose the lesion with respect to the disease, the multi-parametric images required for diagnosing the disease are acquired from an MRI device using the constructed acquisition model. In the above manner, desired multi-parametric images may be acquired in an optimal order using a previously-constructed acquisition model of multi-parametric images relating to a specific disease, and thus it is possible to rapidly acquire multi-parametric images optimized in diagnosing the specific disease.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), CD-ROMs, magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

The apparatuses described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for acquiring multi-parametric images, the apparatus comprising:
    an image analyzer configured to determine a significance level of each of a plurality of multi-parametric images relating to a disease, and to determine an acquisition order of the multi-parametric images and the multi-parametric images to be used in diagnosing the disease; and
    a model constructer configured to construct an acquisition model of the multi-parametric images based on the acquisition order and the multi-parametric images to be used in diagnosing the disease.

2. The apparatus of claim 1, further comprising:
    an image acquirer configured to acquire the multi-parametric images using the constructed acquisition model of the multi-parametric images, wherein the multi-parametric images are magnetic resonance imaging (MRI) images.

3. The apparatus of claim 1, further comprising a model store configured to store the acquisition model of the multi-parametric images.

4. The apparatus of claim 1, wherein:
    the image analyzer comprises
    a Region of Interest (ROI) extractor configured to extract an ROI from each of the plurality of multi-parametric images, and
    a feature extractor configured to extract a feature from the ROI; and
    the image analyzer is further configured to determine the significance level of each of the plurality of multi-parametric images based on the extracted features.

5. The apparatus of claim 3, further comprising a feature analyzer configured to determine whether the extracted feature is significant.

6. The apparatus of claim 4, further comprising:
    an image optimizer configured to normalize the ROI; and
    the feature extractor extracts the feature from the normalized ROI.

7. The apparatus of claim 6, wherein the image optimizer is further configured to remove noise from the normalized ROI, and the feature extractor extracts the feature from the normalized ROI where the noise is removed.

8. The apparatus of claim 4, wherein the features comprises one or more pieces of information about shape, brightness, or boundary.

9. The apparatus of claim 5, wherein the image analyzer determines the significance level of each of the plurality of multi-parametric images based on a number of significant features in each multi-parametric image for diagnosing the disease.

10. The apparatus of claim 9, wherein the number of significant features is determined based on frequency of the features in multi-parametric images of patients suffering from a same disease, wherein the frequency of the features refers to a repetition of the features.

11. The apparatus of claim 9, wherein the image analyzer determines that the multi-parametric image is to be used in diagnosing the disease when the number of significant features in the multi-parametric image exceeds a threshold.

12. The apparatus of claim 4, further comprising an image store configured to store the multi-parametric images.

13. A method for acquiring multi-parametric images, the method comprising:
    determining, at an image analyzer, a significance level of each of a plurality of multi-parametric images relating to a disease;
    determining, based on the determined significance levels, an acquisition order of the multi-parametric images and the multi-parametric images to be used in diagnosing the disease; and
    constructing an acquisition model of the multi-parametric images based on the acquisition order and the multi-parametric images to be used in diagnosing the disease.

14. The method of claim 13, further comprising:
    acquiring the multi-parametric images for diagnosing the disease, by using the constructed acquisition model of the multi-parametric images.

15. The method of claim 13, wherein the determining of the significance level comprises:
    extracting a ROI from each of the multi-parametric images;
    extracting a feature from the ROI; and
    determining the significance level of each of the multi-parametric images based on the extracted feature.

16. The method of claim 15, wherein the determining of the significance level comprises normalizing the ROI, and extracting the feature from the normalized ROI.

17. The method of claim 16, wherein the determining of the significance level further comprises removing noise from the normalized ROI, and extracting the feature from the normalized ROI where noise is removed.

18. The method of claim 15, wherein the features comprises one or more pieces of information about shape, brightness, or boundary.

19. The method of claim 15, wherein the determining of a significance level comprises determining a significance level of each of the plurality of multi-parametric images based on a number of significant features in each multi-parametric image.

20. The method of claim 19, wherein the number of significant features is determined based on frequency of the features in multi-parametric image of multiple patients suffering from a same disease, wherein the frequency of the features refers to a repetition of the features.

21. The method of claim 19, wherein the determining of the significance level comprises, using each multi-parametric image in diagnosing the disease when the number of significant features in the multi-parametric image exceeds a threshold.

22. The method of claim 19, wherein the determining an acquisition order further comprises:
    assigning a weighted value to each of the multi-parametric images;
    determining the acquisition order of the multi-parametric images by multiplying the weighted value by the number of significant features in the multi-parametric image.

23. An apparatus for acquiring multi-parametric images, the apparatus comprising:
    an image analyzer configured to determine an acquisition order of the multi-parametric images and the multi-parametric images to be used in diagnosing the disease;
    a model constructer configured to construct an acquisition model of the multi-parametric images based on the acquisition order and the multi-parametric images to be used in diagnosing the disease; and
    an image acquirer configured to acquire the multi-parametric images based on the acquisition model.

24. The apparatus of claim 23, further comprising a model store configured to store the acquisition model of the multi-parametric images.

25. The apparatus of claim 23, wherein the image analyzer comprises:
- a Region of Interest (ROI) extractor configured to extract an ROI from each of the plurality of multi-parametric images;
- a feature extractor configured to extract a feature from the ROI; and
- a feature analyzer configured to determine whether the extracted feature is significant.

26. The apparatus of claim 25, wherein:
- the image analyzer is configured to determine a significance level of each of the plurality of multi-parametric images based on the based on a number of significant features in each multi-parametric image; and
- the image analyzer is configured to determine the acquisition order and the multi-parametric images to be used in diagnosing the disease based on the significance level of each of the plurality of multi-parametric images.

27. The apparatus of claim 25, further comprising:
- an image optimizer configured to normalize the ROI; and
- the feature extractor extracts the feature from the normalized ROI.

* * * * *